United States Patent [19]

Chen

[11] Patent Number: 5,260,472
[45] Date of Patent: Nov. 9, 1993

[54] EFFICIENT CHEMOENZYMATIC SYNTHESIS OF D-MYO-INOSITOL 1,4,5-TRIPHOSPHATE, D-MYO-INOSITOL 1,3,4-TRIPHOSPHATE, AND D-MYO-INOSITOL 1,3,4,5-TETRAPHOSPHATE

[75] Inventor: Ching-Shih Chen, Wakefield, R.I.

[73] Assignee: The Board of Governors for Higher Education State of Rhode Island and Providence Plantations, Providence, R.I.

[21] Appl. No.: 827,467

[22] Filed: Jan. 29, 1992

[51] Int. Cl.$^5$ .............. C07C 69/03; C07C 69/70; C07C 67/14; C07F 7/18; C07F 7/144; C07F 9/655

[52] U.S. Cl. ............................ 558/161; 558/147; 558/156; 568/833; 549/331; 549/336; 549/341; 536/44

[58] Field of Search ............ 558/147, 156; 568/833

[56] References Cited
FOREIGN PATENT DOCUMENTS
WO91/00258  1/1991  PCT Int'l Appl. ............ 558/161

OTHER PUBLICATIONS

Baudin et al, Halvetica Chimica Acta, vol. 71, pp. 1367 to 1378 (1988).
Garegg et al, Carbohydrate Research, vol. 130, pp. 322 to 326 (1984).
Gigg et al, Carbohydrate Research, vol. 140, pp. C1–C3 (1985).
Guo et al, J. Amer. Chem. Soc., vol. 112, pp. 4942 to 4945 (1990).
Liu et al, Tetrahedron Letters, vol. 30, No. 13, pp. 1617–1620 (1989).
Ozaki et al, Tetrahedron Letters, vol. 27, No. 27, pp. 3157–3160 (1986).
Vacca et al, J. Amer. Chem. Soc., vol. 109, pp. 3478–3479 (1987).

*Primary Examiner*—Floyd D. Higel
*Attorney, Agent, or Firm*—Samuels Gauthier & Stevens

[57] ABSTRACT

Multigram quantities of Ins(1,4,5) $P_3$, Ins(1,3,4) $P_3$, and Ins(1,3,4,5)$P_4$ are prepared in their enantiomerically pure forms from the two enantiomers of 1,2:5,6-di-O-cyclohexylidene myo-inositol. Also, a facile enzymatic preparation is also described of these chiral precursors through enantiospecific deacylation of the corresponding racemic esters is disclosed.

6 Claims, No Drawings

EFFICIENT CHEMOENZYMATIC SYNTHESIS OF D-MYO-INOSITOL 1,4,5-TRIPHOSPHATE, D-MYO-INOSITOL 1,3,4-TRIPHOSPHATE, AND D-MYO-INOSITOL 1,3,4,5-TETRAPHOSPHATE

BACKGROUND AND BRIEF SUMMARY OF THE INVENTION

The important role of Ins(1,4,5)P$_3$ (D-myo-inositol 1,4,5-triphosphate) as a second messenger in transmembrane signal transduction is well documented, M. J. Berridge, and R. F. Irvine, Nature, 341 (1989) 197–201. Once released from its membrane-associated precursor, Ins(1,4,5)P$_3$ undergoes a rapid turnover by two discrete mechanisms mediated by a 5-phosphatase and a 3-kinase, respectively, leading to a number of polyphosphate derivatives, B. V. L. Potter, Natural Product Reports (1990) p. 1–24. These molecules play a role in an intricate metabolic pathway and the physiological function of some of their metabolites remains to be assessed.

With the enzymology and regulation of IP$_3$ cellular metabolism as a basis, efficient synthetic routes to individual inositol polyphosphates have been developed; Y. C. Liu and C. S. Chen, Tetrahedron Lett. 30 (1989) 1617–1620 and D. M. Gou and C. S. Chen, ibid, in press. The strategy entailed a facile biocatalytic route to optically active inositol derivatives which, in turn, served as useful precursors to target molecules.

In this disclosure a unique synthesis is disclosed and exemplified by the preparations of Ins(1,4,5)P$_3$: Chiral synthesis has been reported; S. Ozaki, Y. Watanabe, T. Ogasawara, K. Kondo, N. Shiotani, H. Nishii, and T. Matuki, Tetrahedron Lett., 27 (1986), 3157–3160; C. B. Reese, and J. G. Ward, ibit, 28 (1987) 2309–2312; J. P. Vacca, S. J. DeSolms, and J. R. Hugg, J. An. Chem. Soc. 109 (1987) 3478–3479; C. E. Dreed, R. J. Tuinman, C. J. J. Elie, G. A. van der Marel, and J. H. van Boom, Recl. Trav. Chim. Pays-Bas, 107 (1988) 395–397; S. V. Ley, and F. Sternfeld, Tetrahedron Lett., 29 (1988) 5305–5308; W. Tegge, and C. E. Ballou, Proc. Natl. Acad. Sci. U.S.A., 86 (1989) 94–98; Ins(1,3,4)P$_3$: (D-myo-inositol 1,3,4-triphosphate), (S. Ozaki, M. Kohno, and Y. Wantabe, Chem. Lett. (1988) p. 77–80) ; and Ins(1,3,4,5)P$_4$: D-myo-isositol 1,3,4,5-tetrakis phosphate), (G. Baudin, B. I. Glanzer, K. S. Swaminathan, and A. Vasella, Helv. Chim. Acta, 71 (1988) 1367–1378); in multigram quantities from the optical antipodes of 1,2:5,6-di-O-cyclohexylidene-myo-inositol (1).

DESCRIPTION OF THE PREFERRED EMBODIMENT(S)

Enzymatic Preparation of Chiral Precursors

Treatment of myo-inositol with 1-ethoxycyclohexene yielded a mixture of 1,2:5,6- (1), 1,2:4,5- (2), and 1,2:3,4-di-O-cyclohexylidene-myo-inositol (3) (1.2:1:0.5) in their racemic forms, P. J. Garegg, T. Iversen, R. Johansson, and B. Lindberg, Carbohydr. Res. , 130 (1984) 322–326. These compounds can be readily separated from each other by a combination of flash chromatography and recrystallization. In principle, any of these three derivatives can be employed for the synthesis of inositol phosphates. However, in this study, biocatalytic resolution was applied only to 1 and 2 since they were the major products isolated from the mixture.

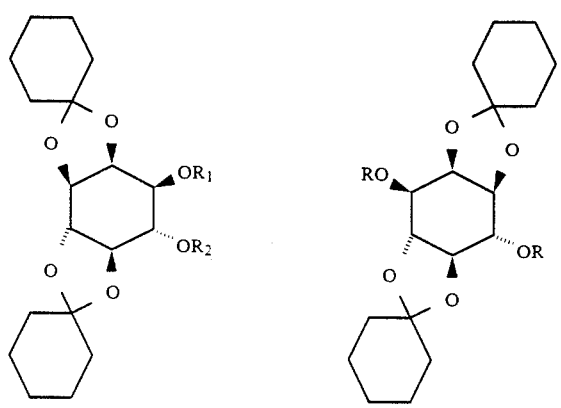

1 R$_1$ = R$_2$ = H
4 R$_1$ = R$_2$ = C(O)CH$_3$
6 R$_1$ = R$_2$ = C(O)C$_3$H$_7$
8 R$_1$ = H; R$_2$ = C(O)CH$_3$
9 R$_1$ = H; R$_2$ = C(O)C$_3$H$_7$

2 R = H
5 R = C(O)CH$_3$
7 R = C(O)C$_3$H$_7$

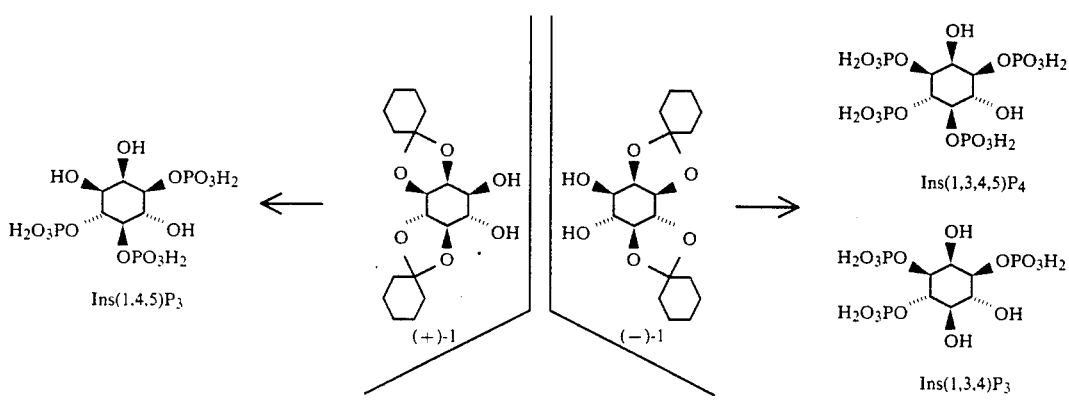

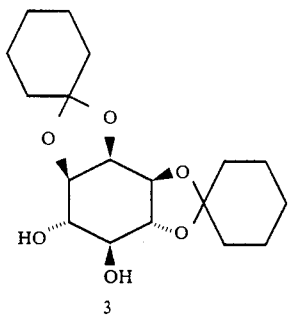

3

(only one enantiomeric form is shown)

In initial experiments, the diacetyl and dibutyryl esters of 1 and 2 (4–7) were exposed to a number of commercial hydrolases including esterases, lipases, and proteases (Esterases included pig liver esterase and cholesterol esterase, Lipases included crude lipase. Preparations from porcine pancreas, Candidacylindracea, *Aspergillus niger, Geotrichum candidum, Humicola lanuginosa, Mucor meihei,* Pseudomonas sp., *Rhizopus niveus* and *Rhizopus oryzae.* Proteases included chymotrypsin, thermolysin and proteases from *Aspergillus oryzae, Aspergillus sojae, Aspergillus satoi,* Rhizopus sp. and *Streptomyces caeapitosus*). It was found that while 4 and 6 were susceptible to deacylation by virtually all the enzymes tested, the esters of 2 (5 and 7) appeared to be resistant to enzymatic cleavage, yielding very small amounts of products even after long incubations. Different degrees of regio- and enantio-selectivity were noted with different enzymes toward 4 and 6. Among the enzymes examined, cholesterol esterase (CE) and porcine pancreatic lipase (PPL) were of particular interest in light of their high degree of stereochemical discrimination. Sequential enzymatic hydrolysis of the diacetyl ester 4 with CE furnished nearly equal amounts of the monoacyl ester 8 and diol 1 with ee values of 0.86 and 0.85, respectively. In contrast, when the dibutyryl ester 6 was treated with CE or PPL, optically active diol 1 (ee>0.98) accompanied with minute quantities of the monoester 9 (ee not determined) was obtained in low yields. The size of the acyl substituent (acetyl vs. butyryl) affected not only the stereochemical outcome but also product distribution. Presumably, this resulted from the differences in the relative deacylation rates for the mono- and di-acyl esters (Z. W. Guo, S. H. Wu, C. S. Chen, G. Girdaukas, and C. J. Sih, J. Am. Chem. Soc., 112(1990) 4942–4945). Thus, for the diacetyl derivative (4), the two consecutive hydrolytic rates were of the same order of magnitude. By comparison, the deacylation rate for the dibutyryl ester (6) was much slower than that for the monobutyrate (9) probably due to steric hindrance at the target site.

| Substrate | Enzyme | Major Products | |
|---|---|---|---|
| 4 (1 g) | C.E. (120 units) (t = 168 h) | 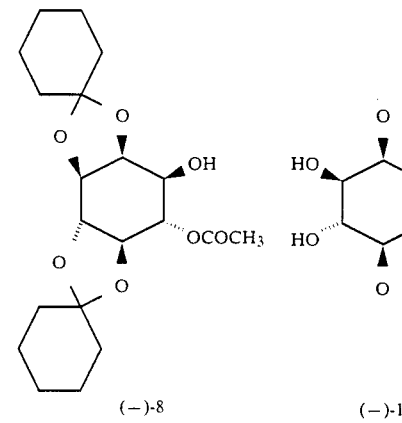 (−)-8 e.e. 0.86 Recovery 345 mg | 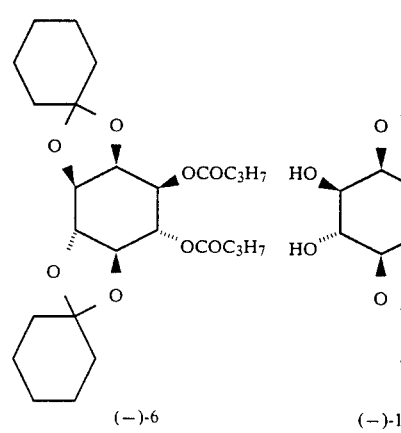 (−)-1 0.85 412 mg |
| 6 (1 g) | | (−)-6 | (−)-1 |

| Substrate | Enzyme | Major Products | | |
|---|---|---|---|---|
| | C.E. | e.e. | 0.12 | >0.98 |
| | (120 units) | Recovery | 850 mg | 95 mg |
| | (t = 168 h) | | | |
| | PPL | e.e. | 0.13 | >0.98 |
| | (500 mg) | Recovery | 870 mg | 82 mg |
| | (t = 168 h) | | | |

*The reaction conditions are described under "Examples".

Although these biocatalyzed deacylations were effected with high stereochemical selection, the reactions were sluggish in part due to poor aqueous solubility and intrinsic steric hindrance. Consequently, excess amounts of enzymes and prolonged incubations were necessary to attain satisfactory conversions. To circumvent this problem, we examined the enantiospecific hydrolysis of the monobutyryl ester 9, a compound with minimized steric congestion and improved solubility. This compound could be obtained in fair yields via stannylidene-activated regioselective acylation (N. Nagashima, and M. Ohno, Chem. Lett. (1987) 141-144) of 1. As anticipated, both CE and PPL readily hydrolyzed 9 to afford optically active 1 with satisfactory enantiomeric purity (Scheme 2). It is worthy to note that although 9 is a monoacyl ester of a vicinal diol, no 1,2-acyl migration took place during the enzymatic reactions.

| Enzyme (amount) | Conversion (%)$^a$ (time) | ee(S) | ee(P) | $E^b$ |
|---|---|---|---|---|
| C.E. (120 units) | 48 (44 h) | 0.86 | 0.93 | 79 |
| PPL (500 mg) | 52 (48 h) | 0.95 | 0.88 | 58 |

$^a$The incubation conditions are described under "Examples";
$^b$The enantiomeric ratio (E) is calculated from $E = \ln\{1 - C[1 + ee(P)]\}/\ln\{1 - C[1 - ee(P)]\}$ where C is the conversion and ee(P) is the ee value of product.

Even though PPL showed slightly lower antipodal differentiation compared to CE, it was used throughout this study because of its low cost and ready availability. Accordingly, both enantiomers of 1 with optical purity greater than 95% were obtained in good yields after recrystallization.

Alternatively, chiral 1 could be obtained by the chromatographic separation of the corresponding dimenthoxycarbonyl diastereomers, followed by alkaline hydrolysis (Y. C. Liu, and C. S. Chen, Tetrahedron Lett, 30 (1989) 1617-1620). This chemical process, although tedious, is especially useful when small quantities of chiral 1 are needed.

Synthesis of Ins(1,4,5)P$_3$ from (+)−1

Scheme 3

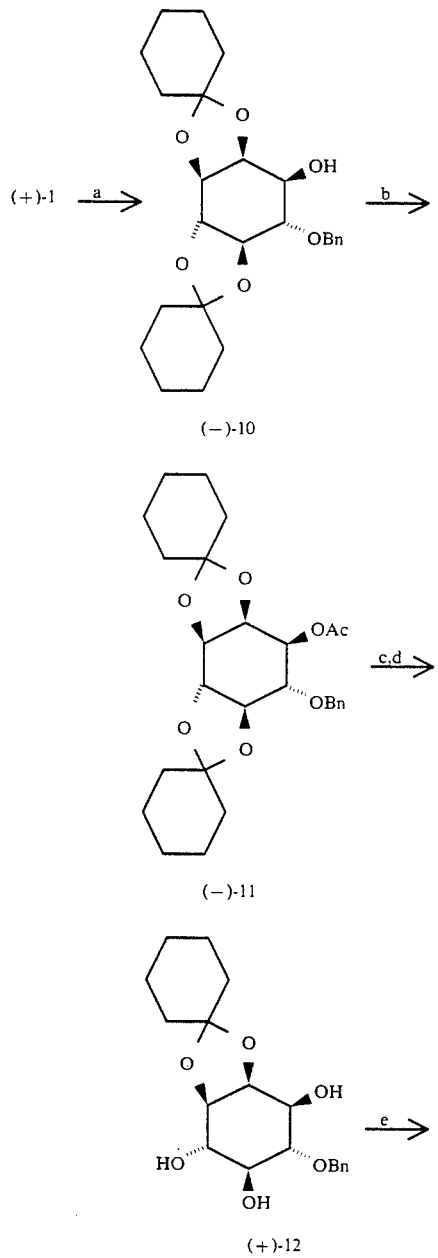

-continued
Scheme 3

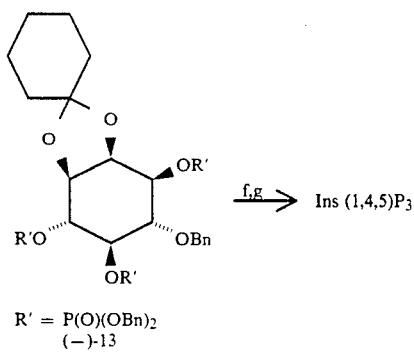

R' = P(O)(OBn)$_2$
(−)-13 a n-Bu$_2$SnO, BnBr, CsF; b Ac$_2$O, DMAP;
c CH$_3$COCl/CH$_3$OH—CH$_2$Cl$_2$; d 1N KOH/CH$_3$OH;
e (BnO)$_2$P—N(iPr)$_2$, 1-H-Tetrazole, MCPBA;
f Pd/C, H$_2$, 95% EtOH; g CH$_3$CO$_2$H The utility of (+)-1 as a chiral precursor is clearly demonstrated by the straightforward synthesis of Ins(1,4,5)P$_3$ depicted in Scheme 3. Stannylidene-activated regioselective benzylation (N. Nagashima, and M. Ohno, Chem. Lett. (1987) 141-144) of (+)−1 afforded (−)−10 in good yield. However, direct acid-catalyzed hydrolysis of the trans-ketal of 10 failed to yield the desired triol 12 in good yield. Instead, an equimolar mixture of 12 and 12a was obtained. The latter compound apparently resulted from acid-catalyzed migration of the cyclohexylidene group. In order to circumvent this problem, (−)−10 was acetylated to give (−)−11. This fully protected derivative, upon selective removal of the trans-cyclohexylidene ring and subsequent base hydolysis of the acetate function furnished precursor (+)−12. Phosphorylation of the triol by the phosphoramidite method (K. L. Yu, B. Fraser-Reid, Tetrahedron Lett., 29 (1988) 979-982) followed by debenzylation and removal of the cis-ketal, gave Ins(1,4,5)P$_3$ with an overall yield of 45% based on (+)−1.

Synthesis of Ins(1,3,4)P$_3$ and Ins(1,3,4,5)P$_4$ from (−)−1

While (+)−1 proved to be a useful intermediate for the synthesis of Ins(1,4,5)P$_3$, retrosynthetic analysis indicated that its enantiomer (−)−1 could also be of practical use to prepare Ins(1,3,4)P$_3$ and Ins(1,3,4,5)P$_4$.

Allylation of (−)−1 and subsequent selective removal of the trans-cyclohexylidene function afforded a key intermediate (+)−14. This could be used as a common precursor to Ins(1,3,4,5)P$_4$ and Ins(1,3,4)P$_3$. While selective 6-O-benzylation led to the former, 5,6-di-O-benzylation afforded the latter as outlined in Scheme 4.

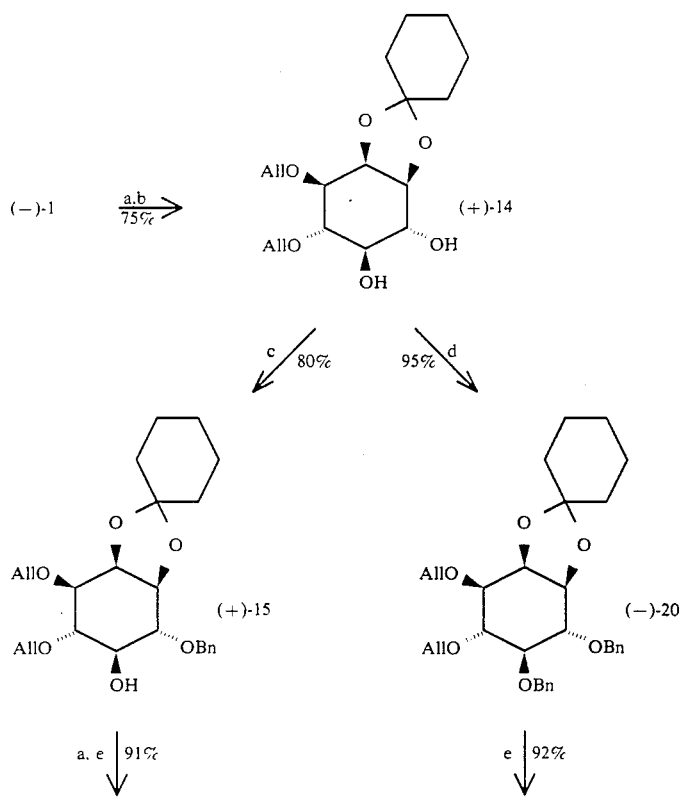

Scheme 4

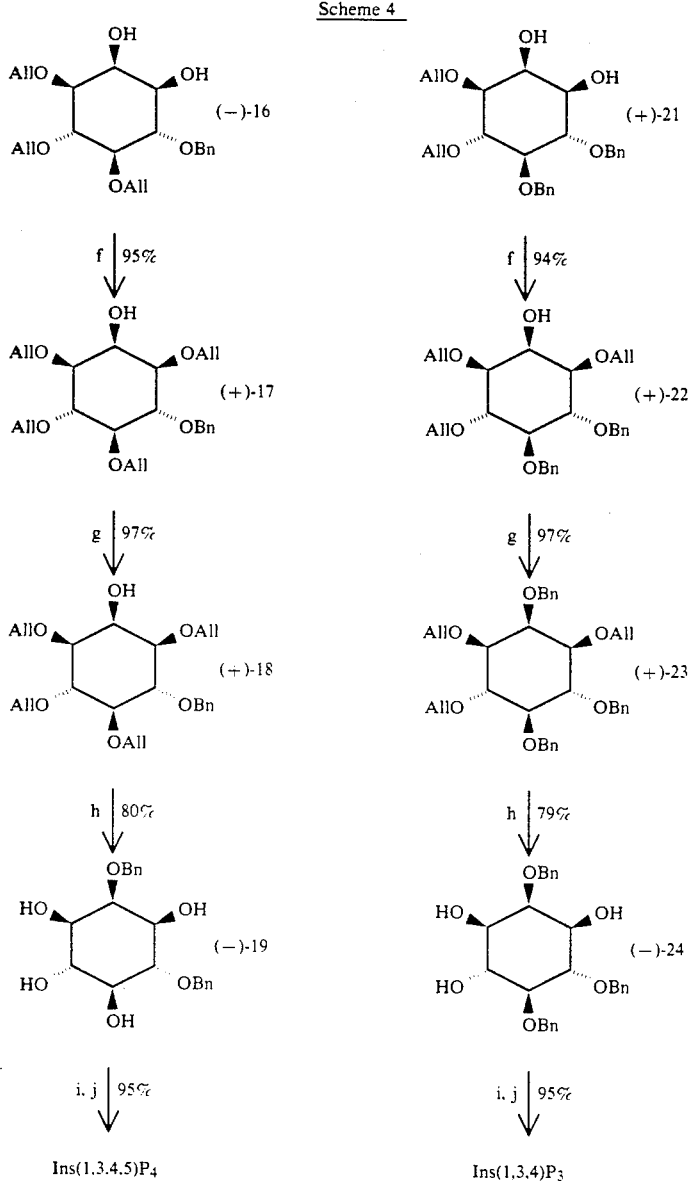

a AllBr/NaH/DMF; b CH$_3$COCl/CH$_3$OH—CH$_2$Cl$_2$;
c n-Bu$_2$SnO, BnBr, CsF; d BnBr/NaH/DMF;
e CH$_3$COCl/CH$_3$OH—CH$_2$Cl$_2$;
f n-Bu$_2$SnO, AllBr, CsF; g BnBr/NaH/DMF;
h Pd(C)/p-TsOH/CH$_3$OH—H$_2$O;
i (BnO)$_2$P—N(iPr)$_2$/1-H-Tetrazole/MCPBA; j Pd/C, H$_2$, 60% EtOH.

Regioselective benzylation at the C-6 position of (+)−14 via the corresponding O-stannylene acetal yielded intermediate (+)−15 whose allylation at the C-5 hydroxyl group followed by the removal of the 1,2-cyclohexylidene ring gave (−)−16. Sequential regioselective allylation of (−)−16 at the C-1 position, followed by benzylation at the C-2 hydroxyl group, furnished the fully protected derivative (+)−18. Deallylation was carried out with 10% Pd/C and p-toluenesulfonic acid to provide derivative (−)−19. This tetrol was then subjected to tandem phosphorylation and debenzylation to give the target molecule Ins(1,3,4,5)P$_4$ in overall yield of 38% based on (−)−1.

The synthesis of the other isomer Ins(1,3,4)P$_3$ is also illustrated in Scheme 4. Exhaustive benzylation of (+)−14, followed by acid hydrolysis of the ketal, gave diol (+)−20. Subsequent transformations leading to the target compound were virtually identical to the procedures described for converting 16 to Ins(1,3,4,5)P$_4$. Accordingly, Ins(1,3,4)P$_3$ [hexapotassium salt; [a]D$^{23}$ +13.6°, C=2, H$_2$O (pH 8.2) ] was obtained in 6 steps from 14 with an overall yield of 60%.

Comparison of the optical rotation of Ins (1,3,4)P$_3$ obtained with the literature value (S. Ozaki, M. Kohno, and Y. Watanabe, Chem. Lett. (1988) p. 77–80) hexaammonium salt; [a ]D$^{23}$ −6°, C=0.5, H$_2$O] revealed a discrepancy in sign and magnitude. While the latter can be accounted for based on difference in molecular weight, the former appears to be irreconcilable. Unfortunately, no additional information concerning chiral Ins(1,3,4)P$_3$ is available (b) the almost identical rotation for its immediate precursor (−)−2,5,6-tri-O-benzyl-myo-inositol (24) ([a]D$^{23}$ −25.4°C=0.5, CHCl$_3$) to that reported in the literature ([a]D$^{23}$ −27°, CHCl$_3$), T. Desai, A. Fernandez, J. Gigg, R. Gigg, C. Jaramilo, S. Payne, S. Penades, and N. Schnetz in Inositol Phosphates and Derivatives, A. B. Reitz, Ed.; ACS Symposium Series 463, American Chemical Society, Washington, D.C., 1991; p. 86–102.

The syntheses of the invention clearly demonstrate the versatility of the synthetic strategy. With both enantiomers of 1 on hand, virtually all inositol polyphosphates can be readily prepared. Although the synthetic strategy is described with reference to the following examples, the strategy is also applicable to other bioactive molecules.

EXAMPLES

General methods. —$^1$H and $^{31}$ NMR spectra were recorded on a Bruker AM-300 spectrometer. Optical rotations were determined with a Rudolph Autopol III polarimeter for solutions in the indicated solvent. High-pressure liquid chromatography was performed using a Model 501 pump (Waters Associates) equipped with a Rheodyne injector and a Model 481 UV/Vis detector (Waters Associates). Cholesterol esterase and crude porcine pancreatic lipase powder (Type II) were purchased from Sigma Chemical Co.,, and the enzyme units were defined accordingly. All other chemicals and solvents of the highest quality grade available were purchased from Aldrich Chemical Co. Racemic 1-3 were prepared according to the procedure reported by Garegg et al., P. J. Garegg, T. Iversen, R. Johansson, and B. Lindberg, Carbhydr. Res., 130 (1984) 322-326. Peracetylation and perbutyrylation of 1 and 2 were carried out according to standard methods.

(±)−6-butyryl -1,2:4,5-Di-O-cyclohexylidene-myo-inositol (9). A mixture of (±)−1 (15 g, 44 mmol), dibutyltin oxide (12 g, 48.4 mmol), and toluene (100 ml) were refluxed with azeotrophic removal of water for 2.5 h, and then concentrated to dryness under reduced pressure. To the residue were added N,N-dimethylformamide (80 ml), cesium fluoride (13.8 g, 88 mmol), and butyryl chloride (4.8 ml, 46 mmol) at −410° C, and the mixture was stirred at 23° C. overnight. The solution was diluted with methylene chloride (200 ml), washed with saturated sodium chloride solution, dried over sodium sulfate, and concentrated. Column chromatography of the crude residue (hexane-ethyl ether, 20:1 to 1:1) gave 9 (10.9 g, 60%). $^1$H NMR (CDCl$_3$): 0.9 (t, 3H, J=6Hz), 1.0–2.5 (m, 24H), 3.0–3.2 (m, 1H), 3.4–3.6 (m, 1H), 3.7–4.1 (m, 2H), 4.2–4.7 (m, 2H), 4.8–5.0 (m, 1H).

General Procedure for Biocatalytic Resolution—The substrate (1 g), dissolved in DMF (7 ml), was introduced dropwise to 0.1 M potassium phosphate buffer (PH 7.4, 70 ml) with vigorous stirring. The solution was subjected to homogenization to give a fine suspension. The reaction was initiated by adding the indicated amount of enzyme (Scheme 1 and 2). The mixture was vigorously stirred at 23° C., and the extent of reaction was monitored by thin layer chromatography. The reaction was terminated by extracting the solution with an equal volume of ethyl acetate (×2). The combined organic fractions were dried and concentrated. The residue was chromatographed over a silica gel column (hexane-ethyl acetate,, 15:1 to 4:1), and the enantiomeric excess of each fraction was determined according to the procedure described below. The diacyl esters were treated with 1 N NaOH/CH$_3$OH (23° C., 3 h) to yield 1 for optical purity determination.

Large Scale Preparation of Optically Active 1—Racemic 9 (15 g) was suspended in the buffer solution (2 L) containing 7 g of crude PPL powder according to the aforementioned method. After vigorously stirring the mixture at 23° C. for 48 h, the reaction was terminated by extracting the solution with an equal volume of ethyl acetate (×2). The organic layer was dried and concentrated, and the residue was chromatographed over a silica gel column to afford (−)−1 (5.6 g; 88% ee; [a ]D$^{23}$ −16.2°, C=1, CHCl$_3$) and (−)−9 (6.5 g; 95% ee; [a]D$^{23}$ −14.2°, C=0.45 CHCl$_3$).

Enantiomeric Purity Determination—The antipodal alcohols, 1, 8, and 9, were treated with (S)-(−)-2-methoxy-2-(trifluoromethyl)-phenylacetyl (MTPA) chloride to form the corresponding MTPA esters. The MTPA diastereomers were analyzed by HPLC using two silica gel columns (10 mm) in tandem (2×4.6 mm ×25 cm) with hexane-ether (5:1) as the mobile phase at a flow rate of 1 ml/min. The retention times were: 1 di-MTPA ester, (+): 16 min; (−): 22.5 min; 8 MTPA ester, (−): 15.5 min, (+): 17.2 min; 9 MTPA ester, (−): 17.6 min, (+)-23.3 min.

(−)-6-O-Benzyl-2,3:4,5-di-O-cyclohexylidene-myo-inositol (10). The procedure for regioselective benzylation of (+)-1 (5.8 g, 16.6 mmol) was identical to that described for 9 except that butyryl chloride was replaced by an equal amount of benzyl bromide (4.5 ml, 38 mmol), to afford (−)-10 (6.1 g, 84%). $^1$H NMR (CDCl$_3$): 1.44–1.75 (m, 20H), 2.65-2.66 (d, 1H, J=1.5 Hz), 3.58 (dd, 1H, J=7.8 Hz), 3.93 (dd, 1H, J=2 Hz), 4.06–4.07 (m, 1H), 4.23 (dd, 1H, J=7.6 Hz), 4.35–4.40 (t, 1H, J=7.5 Hz), 4.46 (dd, 1H, J=3.6 Hz), 4.75 (q, 2H, J=11.8, 35 Hz), 7.28–7.43 (m, 5H); [a ]D$^{23}$ −4° (C=1.6, CHCl$_3$).

(−)-1-Acetyl-6-benzyl-2,3:4,5-di-O-cyclohexylidene-myo-inositol (11)—Compound (−)10 (6 g, 14 mmol) in methylene chloride (50 ml) was acetylated with acetic anhydride (4.5 ml, 42 mmol), triethylamine (12 ml, 126 mmol), and a catalytic amount of N,N-dimethylaminopyridine (122 mg, 1 mmol) at 23° C. for 4 h. The reaction mixture was washed with aqueous sodium hydrogencarbonate and water, dried, and concentrated. The residue was subjected to column chromatography (hexane-ethyl ether, 15:1) to give the title compound 11 (6.6 g, 99%). $^1$H NMR (CDCl$_3$): 1.42–1.68 (m, 20H), 2.14 (s, 3H), 3.63 (dd, 1H, J=7.8 Hz), 3.81 (dd, 1H, J=2.4 Hz), 4.04 (dd, 1H, J=7.8 Hz), 4.39 (t, 1H, J=7.3 Hz), 4.52 (dd, 1H, J=1.2, 4.8 Hz), 4.78 (s, 2H) 5.28–5.31 (dd, 1H, J=2.4, 3.9 Hz), 7.28–7.38 (m, 5H); [a]D$^{23}$ −15.3° (C=0.4, CHCl$_3$).

(+)-6-O-Benzyl-2,3-O-cyclohexylidene-myo-inositol (12). A solution of (−)-11 (6 g, 12.6 mmol) in methylene chloride-methanol (1:1, 150 ml) was treated with acetyl chloride (0.5 ml, 6 mmol), and the reaction mixture was stirred at 23° C. for 40 min. Triethylamine (1. 7 ml, 12 mmol) was then added, and the solution was concentrated. The crude residue was treated with methanolic 1M potassium hydroxide (15 ml) for 1 h at 23° C. After removing the solvent under reduced pressure, the crude product was chromatographed (methylene chloride-ethyl ether-ethanol, 1:8:1) to yield (+)-12 (3.2 g, 72%). $^1$H NMR (CDCl$_3$): 1.35–1.61 (m, 10H), 3.10–3.18 (m, 1H), 3.34–3.50 (m, 3H), 3.68–3.74 (m, 1H), 3.82–3.86 (t, 1H, J=6.2 Hz), 4.16–4.19 (t, 1H, J=9 Hz), 4.69–4.78 (q, 2H, J=12, 15 Hz), 4.86–4.87 (d, 1H, J=3 Hz), 4.96 (s, 1H), 4.97–4.98 (d, 1H, J=2 Hz), 7.22–7.42 (m, 5H); [a]$D^{23}$ +24° (C=0.2, CHCl$_3$).

(−)-6-O-benzyl-2,3-O-cyclohexylidene-myo-inositol-1,4,5-(hexabenzyl)triphosphate (13). Tetrazole (3.6 g, 51 mmol) and N,N-diisopropyl dibenzylphosphoramidite (17.8 g, 51 mol) in methylene chloride (100 ml) was stirred under a blanket of argon at 23° C. for 1h, and (+)-12 (3 g, 8.6 mmol) was added in one portion. The solution was kept under the same conditions for another 12 h, cooled to −40° C., and then treated with triethylamine (14 ml, 100 mmol) and m-chloroperbenzoic acid (50% purity, 17.8 g, 51 mmol). After stirring at −40° C. for 30 min, the mixture was allowed to attain room temperature, and was diluted with methylene chloride (100 ml). The solution was then washed with aqueous sodium sulfite, aqueous sodium hydrogencarbonate and water, dried, and concentrated. Chromatographic purification of the residue (hexane-ethyl acetate, 20:1 to 2:1) furnished the title compound (−)-13 in 97% yield. $^1$H NMR (CDCl$_3$): 1.34–1.78 (m, 10H), 4.18–4.22 (m, 1H), 4.26–4.33 (m, 1H), 4.63–4.71 (m, 3H), 4.77–4.89 (m, 4H), 4.91–5.17 (m, 11H), 7.13–7.34 (m, 35H); [a]$D^{23}$ −6.0°, (C=1.1, CHCl$_3$).

D-myo-inositol 1,4,5-triphosphate (Ins(1,4,5)P$_3$). Triphosphate (−)-13 (9 g, 8 mmol) and 10% Pd/C (4.5 g) in 90% ethanol was shaken on a mini-Parr apparatus under an atmosphere of H$_2$ (50 psig). After 5 h, the solution was filtered and concentrated. The residue was dissolved in acetic acid-water (1:1, 8 ml), stirred at 23° C. for 4 h, and 70 ml of absolute ethanol was added. The solution was concentrated to dryness, and the residue was titrated with methylene chloride-ether (1:1). The white precipitate thus formed was dissolved in a minimal amount of water, and 6 equivalents of 1 M potassium hydroxide was added. The solution was diluted with absolute ethanol (80 ml) to precipitate the product. The precipitate was dissolved in water (10 ml), and lyophilized to afford the title molecule Ins(1,4,5)P$_3$ as a hexa-potassium salt in 98% yield. $^1$H NMR (D$_2$O): 3.54–3.58 (dd, 1H, J=3, 9.3 Hz), 3.66–3.79 (m, 3H), 3.95–4.04 (m, 1H), 4.19 (br. s, 1H) ; $^{31}$P NMR (D$_2$O, H$_3$PO$_4$ as external standard): 4.67 (1P), 4.49 (1P), 2.86 (1P); [a]$D^{23}$ −24.4°, (C=0.5, H$_2$O, pH 9.3).

(+)-3,4-di-O-allyl-1,2-O-cyclohexylidene-myo-inositol (14). A solution of compound (−)-1 (6.7 g, 19.7 mmol) in DMF (50 ml) was treated with sodium hydride (2.36 g, 78.8 mmol) and allyl bromide (6 ml, 69 mmol) for 3 h at 23° C. Excess of allyl bromide was destroyed with methanol, and the mixture was concentrated. The residue was dissolved in methylene chloride (150 ml), washed with water, dried, and concentrated. Column chromatography of the product (hexane-ethyl ether, 15:1) gave (+)-3,4-di-O-allyl-1,2:5,6-di-O-cyclohexylidene-myo-inositol (7.6 g, 92%). $^1$H NMR (CDCl$_3$): 1.38–1.76 (m, 20H), 3.44 (dd, 1H, J=7.5 Hz), 3.65 (t, 1H, J=3Hz), 3.77 (dd, 1H, J=3Hz), 4.06–4.25 (m, 5H), 4.31 (t, 1H, J=9Hz), 4.37 (dd, 1H, J=3.6 Hz), 5.15–5.21 (m, 2H), 5.26–5.30 (m, 1H), 5.32–5.35 (m, 1H), 5.83–5.89 (m, 2H); [a]$D^{23}$ +6.5°, (C=0.4, CHCl$_3$).

The foregoing compound was subjected to selective hydrolysis of the trans-cyclohexylidene group as described for 12, to yield 14 (5.1 g, 82%). $^1$H NMR (CDCl$_3$): 1.36–1.78 (m, 10H), 3.24–3.35 (m, 3H), 3.55–3.62 (m, 2H), 3.72 (dd, 1H, J=7.8 Hz), 3.97 (dd, 1H, J=6 Hz), 4.19–4.22 (m, 2H), 4.26 (m, 1H), 4.37–4.44 (m, 2H), 5.15–5.22 (m, 2H), 5.26–5.29 (m, 1H), 5.32–5.34 (m, 1H), 5.86–6.03 (m, 2H); [a]$D^{23}$ +1.6°, (C=1.9, CHCl$_3$).

(+)-3,4-Di-O-allyl-6-O-benzyl-1,2-O-cyclohexylidene-myo-inositol (15). Compound (+) -14 (3 g, 7 mmol) underwent regioselective benzylation as described for 10, to furnish (+)-15 (3.04 g, 80%). $^1$H NMR (CDCl$_3$): 1.46–1.81 (m, 10H), 2.75 (br. s, 1H), 3.46–3.49 (m, 1H), 3.60–3.73 (m, 3H), 4.16 (dd, J=6 Hz), 4.22–4.30 (m, 3H), 4.34–4.43 (m, 2H), 4.75 (d, 1H, J=12 Hz), 4.97 (d, 1H, J=12 Hz), 5.18–5.24 (m, 2H), 5.29–5.30 (m, 1H), 5.34–5.36 (m, 1H), 5.90–6.05 (m, 2H), 7.24–7.42 (m, 5H); [a]$D^{23}$ +13.6°, (C=1.5, CHCl$_3$).

(−)-3,4,5-Tri-O-allyl-6-O-benzyl-myo-inositol (16). Allylation of compound (+)-15 (2.95 g, 6.9 mmol) was carried out with allyl bromide as described for 14, to generate (−)-3,4,5-tri-O-allyl-6-O-benzyl-1,2-O-cyclohexylidene-myo-inositol (3.18 g, 98%). $^1$H NMR (CDCl$_3$): 1.45–1.76 (m, 10H), 3.23 (dd, 1H, J=8.4 Hz), 3.54 (dd, 1H, J=3.6 Hz), 3.66–3.73 (m, 2H), 4.09 (dd, 1H, J=5.4 Hz), 4.21–4.38 (m, 7H), 4.81 (q, 2H, J=7.4, 36 Hz), 5.13–5.21 (m, 3H) 5.24–5.34 (m, 3H), 5.89–6.04 (m, 3H), 7.24–7.42 (m, 5H); [a]$D^{23}$ −9.2° (C=1.5, CHCl$_3$).

The foregoing compound (3.18 g, 6.77 mmol) was treated with acetyl chloride (0.2 ml, 2.6 mmol) in methylene chloride-methanol (1:1, 75 ml) at 23° C. for 1 h. The solution was concentrated, and the residue was purified by column chromatography (hexane-ethyl acetate, 20:1 to 2:1) to afford the title molecule (−)-16 (2.45 g, 93%). $^1$H NMR (CDCl$_3$): 2.66 (d, 1H, J=3.6 Hz), 2.72 (d, 1H, J=1.2 Hz), 3.22–3.29 (m, 2H), 3.40–3.51 (m, 1H), 3.67–3.76 (m, 2H), 4.12–4.19 (m, 3H), 4.21–4.41 (m, 4H), 4.84 (q, 2H, J=7.5, 36 Hz), 5.13–5.34 (m, 6H), 5.86–6.04 (m, 3H), 7.27–7.40 (m, 5H); [a]$D^{23}$ −10° (C=2, CHCl$_3$).

(+)-1,3,4,5-Tetra-O-allyl-6-O-benzyl-myo-inositol (17). Regioselective allylation of (−)-16 (2.4 g, 6.2 mmol) with Bu$_2$SnO and CsF was achieved as described for 9, to yield (+)-17 (2.5 g, 95%). $^1$H NMR (CDCl$_3$) : 2.48 (br. s, 1H), 3.10–3.27 (m, 3H), 3.66–3.75 (m, 1H), 3.83 (t, 1H, J=9.6 Hz), 4.16–4.20 (m, 5H), 4.28–4.32 (m, 4H), 4.81 (q, 2H, J=10.8, 13 Hz), 5.12–5.21 (m, 4M), 5.23–5.34 (m, 4H), 5.87–6.04 (m, 4H), 7.25–7.39 (m, 5H); [a]$D^{23}$ +10.7° (C=3.1, CHCl$_3$). (+)-1,3,4,5-Tetra-O-allyl-2,6-di-O-benzyl-myo-inositol (18). A solution of compound (+)-17 (2.5 g, 5.8 mmol) i DMF (20 ml) was treated with sodium hydride (0.349 g, 11.8 mmol) and benzyl bromide (1.1 ml, 8.7 mmol) for 8 h at 23° C. Excess of benzyl bromide was destroyed with methanol, and the mixture was concentrated. The residue was dissolved in methylene chloride (100 ml), washed with water, dried, and concentrated. Column chromatography of the product (hexane-ethyl ether, 20:1 to 5:1) gave the title compound (+)-18 (3 g, 97%). $^1$H NMR (CDCl$_3$): 3.11–3.24 (m, 3H), 3.76–3.95 (m, 3H), 4.04–4.99 (m, 4H), 4.24–4.35 (m, 4H), 4.73–4.84 (m, 4H), 5.10–5.17 (m, 4H), 5.21–5.32 (m, 4H), 5.81–6.02 (m, 4H), 7.21–7.43 (m, 10H); [a]$D^{23}$ +0.8° (C=1.1, CHCl$_3$).

(−)-2,6-Di-O-benzyl-myo-inositol (19). A mixture of (+)-18 (3 g, 5.76 mmol), 10% Pd/C, p-toluenesulfonic acid (500 mg, 2.6 mmol) in methanol-water (5:1, 90 ml) was stirred under reflux for 2 h, then filtered, and concentrated. Column chromatography of the residue (ethyl ether-ethanol, 10:1) furnished (−)-19 (1.65 g, 80%). $^1$H NMR (CD$_3$OD): 3.24–3.30 (m, 1H), 3.38 (dd, 1H, J=2.4 Hz), 3.51–3.69 (m, 3H), 3.85–3.86 (m, 1H), 4.77–4.87 (m, 4H), 7.18–7.41 (m, 10H); [a ]$D^{23}$ −29° (C=0.65, EtOH).

D-myo-inositol 1,3,4,5-tetraphosphate (Ins(1,3,4,5)P$_4$). The tetrol (−)-19 (1.6 g, 4.4 mmol) was subjected to phosphorylation with N,N-diisopropyl dibenzylphosphoramidite, tetrazole, and MCPBA as described for compound 13, to yield D-myo-inositol 1,3,4,5-(octabenzyl)tetraphosphate (6 g, 96%). $^1$H NMR (DCCl$_3$): 4.03-4.10 (m, 1H), 4.20-4.31 (m, 2H), 4.40-4.49 (m, 1H), 4.60-5.07 (m, 22H) , 6.94-7.38 (m, 50H); [a]D$^{23}$ −3.5°, (C=2.9, CHCl$_3$).

A solution of the foregoing product (6 g, 5.3 mmol) and 10% Pd/C (3 g) in 60% ethanol was shaken on a mini-Parr apparatus under an atmosphere of H$_2$ (50 psig). After 24 h, the solution was filtered and concentrated. The residue was dissolved in a minimal amount of water, and 8 equivalents of 1M potassium hydroxide was added. The solution was diluted with absolute ethanol (20 ml). The precipitate was dissolved in water (20 ml) , and lyophilized to afford the title molecule Ins(1,3,4,5)P$_4$ as a octa-potassium salt in 99% yield. $^1$H NMR (D$_2$O) 3.69-3.91 (m, 4H), 4.14-4.23 (q, 1H, J=9, 18 Hz) , 4.32 (m, 1H); $^{31}$P NMR (D$_2$O, H$_3$PO$_4$ as external standard) : 2.94 (1P) , 4.58 (1P) , 4.73 (1P) , 5.27 (1P) [a]D$^{23}$ −3.5°, (C=5.5, H$_2$O, pH 8.4). (−)-3,4-Di-O-allyl-5,6-di-O-benzyl-1,2-O-cyclohexylidene-myo-inositol (20). Conventional benzylation of (+)-14 (2 g, 8.8 mmol) was carried out as described for 18, to produce (−)-20 (2.9 g, 95%). $^1$H NMR (CDCl$_3$) 1.54-1.76 (m, 10H), 3.36 (dd, 1H, J=9 Hz), 3.58 (dd, 1H, J=3.9 Hz) , 3.76 (dd, 2 H, J=9 Hz) , 4.14 (dd, 1H, J=5.4 Hz), 4.22-4.32 (m, 4H), 4.36-4.39 (m, 1H), 4.73 (d, 1H, J=11.4 Hz), 4.78 (s, 2H), 4.89 (d, 1H, J=11.4 Hz), 5.13-5.21 (m, 2H) , 5.24-5.28 (m, 1H) , 5.30-5.34 (m, 1H) , 5.88-6.04 (m, 2H), 7.23-7.39 (m, 10H) ; [a]D$^{23}$ −4.5° (C=1.2, CHCl$_3$).

(+)-3,4-Di-O-allyl-5,6-di-O-benzyl-myo-inositol (21). The removal of the cyclohexylidene group of (−)−20 (2.6 g, 5 mmol) was conducted as described for 16, to generate (+)−21 (2 g, 92 %). $^1$H NMR (CDCl$_3$) 2.61 (d, 1H, J=4.2 Hz), 2.67 (s, 1H), 3.31 (dd, 1H, J=3 Hz), 3.40-3.50 (m, 2H), 3.76-3.83 (m, 2H), 4.15-4.20 (m, 3H), 4.28-4.41 (m, 2H), 4.74 (d, 1H, J=11Hz), 4.82 (d, 1H, J=11Hz), 4.94 (t, 2H), 5.15-5.36 (m, 4H), 5.88-6.06 (m, 2H), 7.27-7.37 (m, 10H); [a]$^{23}$ +0.5°, (C=1.2, CHCl$_3$).

(+)-1,3,4-Tri-O-allyl-5,6-di-O-benzyl-myo-inositol (22). Regioselective allylation of (+)−21 (2 g, 4.5 mmol) with Bu$_2$SnO and CsF was achieved as described for 9, to yield (+)−22 (2.1 g, 94%. $^1$H NMR (CDCl$_3$): 2.50 (s, 1H), 3.25-3.34 (m, 2H), 3.39 (t, 1H, J = 12 hz), 3.81 (t, 1H, J=9.6 Hz), 3.91 (t, 1H, J=9.6 hz), 4.20-4.22 (m, 5H), 4.32-4.37 (m, 2H), 4.78-4.89 (m, 4H), 5.13-5.36 (m, 6H), 5.89-6.05 (m, 3H), 7.25-7.37 (m, 10H); [a]D$^{23}$ +23.8° (C=3.3, CHCl$_3$).

(+)-1,3,4-tri-O-allyl-2,5,6-tri-O-benzyl-myo-inositol (23). Conventional benzylation of (+)−22 (2 g, 4.2 mmol) was carried out as described for 18, to produce (+)−23 (2.3 g, 97%). $^1$H NMR (CDCl$_3$): 3.18-3.27 (m, 2H), 3.38 (t, 1H, J=9Hz), 3.89 (dd, 1H, J=9 Hz), 3.97-4.01 (m, 2H), 4.03-4.11 (m, 4H), 4.25-4.41 (m, 2H), 4.76-4.90 (m, 6H), 5.10-5.34 (m, 6H), 5.84-6.04 (m, 3H), 7.22-7.44 (m, 15H); [a]D$^{23}$ +15.5°, (C=0.8, CHCl$_3$).

(−)-2,5,6-tri-O-benzyl-myo-inositol (24). Deallylation of (+)-23 (2.3 g, 4 mmol) was conducted as described for 19, to yield (−)−24 (1.43 g, 79%). $^1$H NMR (CDCl$_3$): 2.39 (d, 1H, J=3 Hz) , 2.49 (br. s, 1H) , 2.64 (br. s, 1H) , 3.32 (t, 1H, J=9 Hz) , 3.44 (d, 1H, J=9 Hz) , 3.57 (d, 1H, J=9Hz) , 3.74-3.85 (m, 2H) , 3.97-3.99 (m, 1H) , 4.74-4.93 (m, 6H) , 7.24-7.35 (m, 15H) [a]D$^{23}$ −25.4°, (C=0.5, CHCl$_3$).

D-myo-Inositol 1,3,4-triphosphate (Ins(1,3,4)P$_3$). The triol (−)−24 (1.4 g, 3.1 mmol) underwent phosphorylation and debenzylation as described for Ins(1,3,4,5)P$_4$, to afford Ins (1,3,4)P$_3$ (1.9 g, 95%). $^1$H NMR (D$_2$O): 3.38 (t, 1H, J=9 Hz), 3.64 (t, 1H, J=9 Hz), 3.73-3.82 (m, 2H), 3.99 (dd, 1H, J=9 Hz), 4.30 (m, 1H); $^{31}$P NMR (D$_2$O, H$_3$PO$_4$ as external standard) : 3.28 (1P), 4.16 (1P), 4.87 (1P); [a]D$^{23}$ +13.6° (c=2, H20, pH 8.2).

The foregoing description has been limited to specific embodiments of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the synthesis of D-myo-inositol 1,4,5-triphosphate which comprises:
    converting 1,2:5,6-di-O-cyclohexylidene myo-inositol into a racemic ester mixture, resolving the racemic ester mixture into its enantiomerically active forms and selecting said active form comprising a chiral precursor of the following formula;

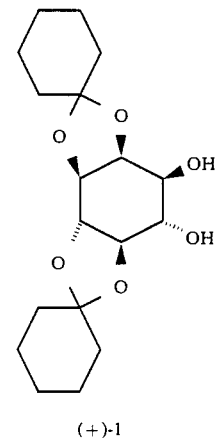

(+)-1 benzylating regioselectively the enantiomer to form a benzylated product of the following formula

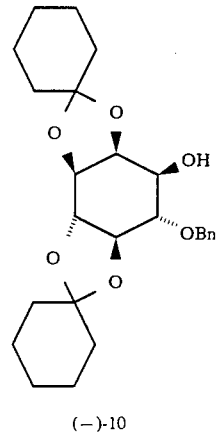

(−)-10 acetylating the benzylated product to form an acetylated compound having a trans-cyclohexylidene ring of the following formula

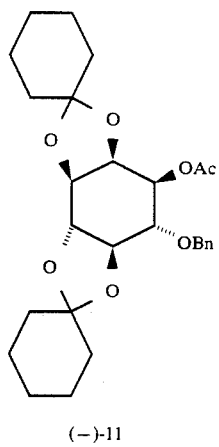

(−)-11 removing the trans-cyclohexylidene ring from the acetylated compound and then hydrolyzing the same to form a triol of the following formula

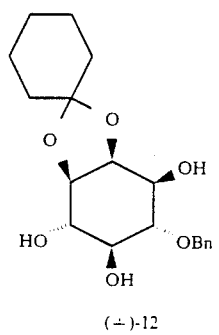

(−)-12 phosphorylating said triol to form

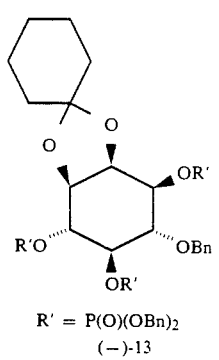

R' = P(O)(OBn)$_2$
(−)-13 and
debenzylating and removing a cis-ketal from said phosphorylated triol to form D-myo-inositol 1,4,5-triphosphate.

2. The method of claim 1 wherein the regioselective benzylation is a stannylidene-activated benzylation.

3. The method of claim 1 wherein the phosphorylation is a phosphoramidite phosphorylation.

4. A method for the synthesis of D-myo-inositol 1,3,4,5-tetraphosphate and D-myo-inositol 1,3,4-triphosphate which comprises:
converting 1,2:5,6-di-O-cyclohexylidene myo-inositol into a racemic ester mixture, resolving the racemic ester mixture into its enantiomerically active forms and selecting said active form comprising a chiral precursor of the following formula;

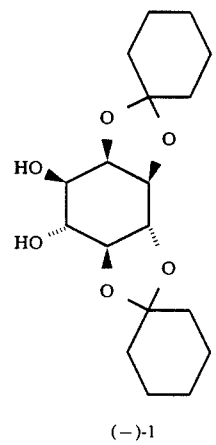

(−)-1 allylating said chiral precursor to form an acetylated product having a trans-cyclohexylidene ring and selectively removing the trans-cyclohexylidene ring to form an intermediate having the composition of

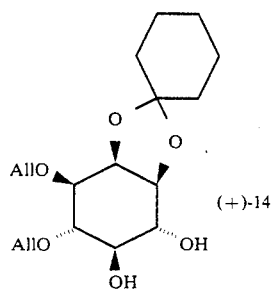

(+)-14

5. The method of claim 4 comprising:
regioselectively benzylating said intermediate to form a benzylated product of

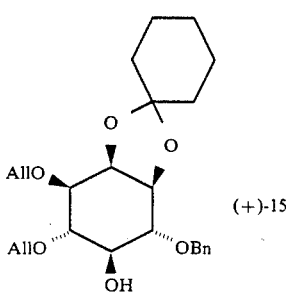

(+)-15 allylating said benzylated product to form an allylated product and removing a 1,2-cyclohexylidene ring from the allylated product to form

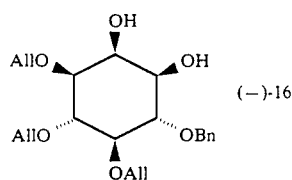

(−)-16 allylating regioselectively the product after the cyclohexylidene ring has been removed to form

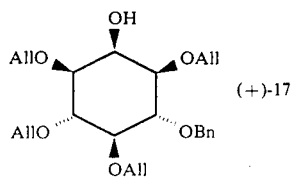

(+)-17 benzylating the regioselectively allylated compound to form a fully protected derivative to form

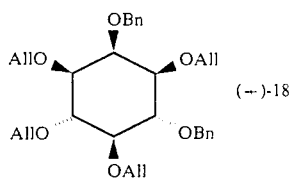

(−)-18 deallylating said derivative to form a tetrol of the formula

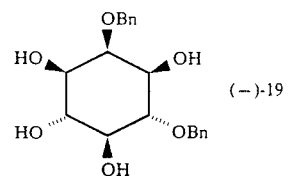

(−)-19 and phosphorylating and debenzylating said tetrol to form D-myo-inositol 1,3,4,5-tetraphosphate.

6. The method of claim 4 comprising:

benzylating said intermediate with subsequent acid hydrolyzing of a ketal of the benzylated compound to form a diol to form

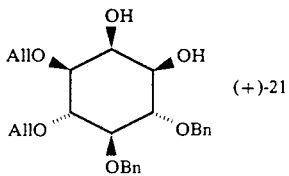

(−)-20 allylating said diol and removing a 1,2-cyclohexylidene ring from the allylated product to form

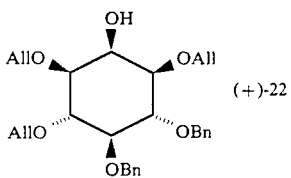

(+)-21 allylating regioselectively the product after the cyclohexylidene ring has been removed to form

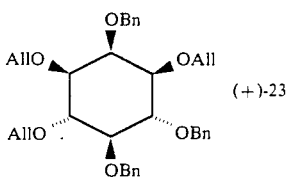

(+)-22 benzylating the regioselectively allylated compound to form a fully protected derivative of the formula

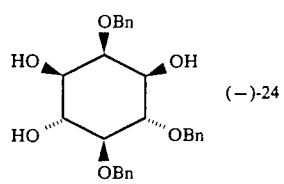

(+)-23 deallylating said derivative to form a tetrol of the formula

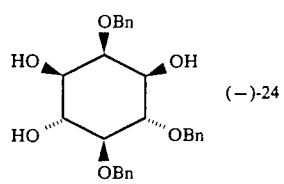

(−)-24 and
phosphorylating and debenzylating said tetrol to form D-myo-inositol 1,3,4-triphosphate.

* * * * *